(12) United States Patent
Thum et al.

(10) Patent No.: US 9,234,220 B2
(45) Date of Patent: Jan. 12, 2016

(54) PROCESS FOR HETEROGENEOUSLY CATALYZED PREPARATION OF CARBOXYLIC ACID DERIVATIVES

(75) Inventors: Oliver Thum, Ratingen (DE); Lutz Hilterhaus, Hamburg (DE); Andreas Liese, Hamburg (DE)

(73) Assignee: Evonik DeGussa GmbH, Essen (DE)

(*) Notice: Subject to any disclaimer, the term of this patent is extended or adjusted under 35 U.S.C. 154(b) by 1333 days.

(21) Appl. No.: 12/354,256

(22) Filed: Jan. 15, 2009

(65) Prior Publication Data

US 2010/0167360 A1   Jul. 1, 2010

(30) Foreign Application Priority Data

Jan. 16, 2008 (DE) .......................... 10 2008 004 725

(51) Int. Cl.
C12P 7/62 (2006.01)
C12M 1/40 (2006.01)
C12M 1/12 (2006.01)

(52) U.S. Cl.
CPC *C12P 7/62* (2013.01); *C12M 21/18* (2013.01); *C12M 25/16* (2013.01)

(58) Field of Classification Search
None
See application file for complete search history.

(56) References Cited

U.S. PATENT DOCUMENTS

| | | | |
|---|---|---|---|
| 2,553,649 A | 2/1981 | Simon | |
| 4,251,631 A | 2/1981 | Simon | |
| 4,921,799 A | 5/1990 | Kitaura et al. | |
| 5,713,965 A | 2/1998 | Foglia et al. | |
| 7,566,795 B2* | 7/2009 | Boaz et al. | 554/214 |
| 7,855,265 B2* | 12/2010 | Thum et al. | 528/31 |
| 2002/0090686 A1 | 7/2002 | Gruning et al. | |
| 2006/0074259 A1 | 4/2006 | Thum et al. | |
| 2007/0184006 A1 | 8/2007 | Ferenz et al. | |
| 2009/0017519 A1 | 1/2009 | Thum et al. | |
| 2009/0062459 A1* | 3/2009 | Thum et al. | 524/588 |
| 2009/0136437 A1 | 5/2009 | Springer et al. | |
| 2009/0181439 A1 | 7/2009 | Thum et al. | |

FOREIGN PATENT DOCUMENTS

| | | |
|---|---|---|
| DE | 25 53 649 | 6/1976 |
| DE | 2553649 A1 | 6/1976 |
| DE | 101 22 551 | 11/2002 |
| EP | 0 413 307 | 2/1991 |

(Continued)

OTHER PUBLICATIONS

Hills, Geoffrey "Industrial Use of Lipases to Produce Fatty Acid Esters" Eur. J. Lipid Sci. Technol. 2003, 105, pp. 601-607 (DOI 10.1002/ejlt.200300853).*

(Continued)

*Primary Examiner* — Louise W Humphrey
*Assistant Examiner* — Aaron J Kosar
(74) *Attorney, Agent, or Firm* — Frommer Lawrence & Haug LLP (57) ABSTRACT

Process for heterogeneously catalyzed preparation of carboxylic acid derivatives using a reactor system comprising at least one reservoir vessel V, feed lines, at least one pump and a reaction vessel R, characterized in that a permanent gas flow through the reaction vessel R is applied through a gas feed line, and in which a reaction chamber in which the heterogeneous catalyst is not introduced in tightly packed form is delimited by at least two filters such that both the mass flow and the gas flow are passed through the reaction chamber.

19 Claims, 5 Drawing Sheets

(56) References Cited

FOREIGN PATENT DOCUMENTS

| EP | 0413307 A1 | 2/1991 |
| EP | 0 670 372 | 9/1995 |
| GB | 1527360 A | 10/1978 |
| WO | WO-0248130 A1 | 6/2002 |

OTHER PUBLICATIONS

Liese, A. "Technical Biocatalysis—From Lab Scale to Industrial Scale" TUHH—BioKatalyse 2021, Oct. 10, 2008, 26 pages.*

Yuguo, Z; Zhao, W; Xiaolong, C "[alpha]-Amylase Production by Bacillus subtilis with Dregs in an External-loop Airlift Bioreactor" Biochemical Engineering Journal 5 (2000) 115-121.*

T.E.S.S. "CELITE®" TM Electronic Search System, 1915 (accessed May 19, 2015), 1 page.*

ChemicalBook "Celite" ChemicalBook.com, retrieved online from <URL:http://www.chemicalbook.com/ChemicalProductProperty_EN_CB9729388.htm>, Dec. 3, 2009, 3 pages.*

Mojovic, Ljiljana et al., "Rhizopus arrhizus lipase-catalyzed interesterification of palm oil midfraction in a gas-lift reactor" Enzyme Microb. Technol, vol. 16, (1994) pp. 159-162.

* cited by examiner

PROCESS FOR HETEROGENEOUSLY CATALYZED PREPARATION OF CARBOXYLIC ACID DERIVATIVES

This application claims benefit under 35 U.S.C. 119(a) of German patent application DE 10 2008 004 725.2, filed on 16 Jan. 2008.

Any foregoing applications including German patent application DE 10 2008 004 725.2, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

The invention relates to a novel process for preparing carboxylic acid derivatives using heterogeneous catalysts.

Carboxylic acid derivatives, for example carboxylic esters or carboxamides, are an important group of chemical compounds. Esters of fatty acids, are, for example, frequently used as the oil phase in cosmetic formulations. To prepare such compounds proceeding from carboxylic acids or activated derivatives, for example acid chlorides, anhydrides or esters of short-chain alcohols, various methods are known. A first overview on this subject can be found in: Becker et al., "Organikum", 22nd edition, Wiley-VCH: 2004, Weinheim, Germany, page 472 ff.

The use of these heterogeneous catalysts has the advantage that they can be removed in a simple manner after the reaction and if appropriate reused Examples of such heterogeneous catalysts are, as well as the solid catalysts which are insoluble in the reaction medium, for example, metal salts, ion exchange resins or catalysts immobilized on suitable supports. Particularly suitable catalysts are those with particle sizes which allow simple and rapid removal from the reaction medium. Frequently, the catalysts used are therefore acidic ion exchange resins, e.g. AMBERLITE IRA 118 (from Rohm and Haas) and enzymes or microorganisms comprising enzymes, which are immobilized on supports. The supports used for enzyme immobilization are frequently ion exchange resins or polymer particles which possess suitable particle size distributions. Examples of these are the commercial products sold under the tradenames NOVOZYM 435, LIPOZYM RM IM or LIPOZYM TL IM from Novozymes A/S, Bagsvaerd, Denmark, or AMANO PS, from Amano, Japan. However, many other methods of obtaining immobilized enzyme preparations have also been described, for example in K. Faber, "Biotransformations in Organic Chemistry", Springer: 2000, Berlin, Deutschland, 384ff., J. Am. Chem. Soc. 1999, 121, 9487-9496, J. Mol. Catal. B, 2005, 35, 93-99, or DE 10 2007 031689.7 (EP 2 011 865 A1).

A further condition for ensuring reusability is the minimization of the mechanical forces which act on the catalysts used and cause disintegration of the support and hence a significant particle size reduction, as a result of which the requirement for easy removability is no longer satisfied and great activity losses are often also observed. Such forces occur in particular when conventional stirred reactors are used. For example, DE 10 2007 031689.7 (U.S. application Ser. No. 12/168,350) describes the particle size reduction which occurs in enzyme immobilizates after use in stirred flasks. Since the process according to the invention can dispense with the use of stirrers in the reaction chamber, and since the mixing is ensured by the gas supply, the mechanical stress, but also the thermal stress on the catalyst particles induced by the stirrer, is reduced to a minimum. These are fundamental prerequisites for reusability of the catalyst, or the preferably supported enzymatic system.

One means of improving the mechanical stability of the catalysts used lies in the use of a fixed bed reactor. Eur. J. Lipid Sci. Technol. 2003, 105, 601-607 describes, for example, the use of a fixed bed reactor for performing lipase-catalysed esterifications. The catalyst is used here in the form of a packed bed and the reaction mixture is pumped out of a reservoir vessel in circulation through the fixed bed until the desired conversion has been attained. An additional filtration step for removing the biocatalyst is not necessary since it is permanently retained in the fixed bed.

The compartmentalization of the system obtained through the use of the fixed bed, i.e. the spatial separation of the relatively small catalyst vessel from the relatively large reservoir vessel, gives rise to a further advantage: for any cleaning of the system which is required or the exchange of the catalyst, only the fixed bed has to be opened, which, for system-related reasons, is significantly smaller and more readily accessible than a stirred vessel which would have to have the same volume as the reservoir vessel used. Specifically on the production scale, i.e. in the case of a batch size in the region of several tonnes, cleaning of such reactor vessels to remove catalyst particles is exceptionally laborious and inconvenient.

However, a disadvantage of this process is the restriction to low-viscosity homogeneous reaction mixtures, since high-viscosity mixtures or suspensions cannot be conveyed through a fixed bed owing to the high pressure drop. The esters described in Eur. J. Lipid Sci. Technol. 2003, 105, 601-607 or Tens. Surfact. Det. 2004, 41, 287-290 possess, for example, viscosities of below 10 mPas at reaction temperature. The attempt to process higher-viscosity raw materials, for example polyglycerol-3, which possesses a viscosity of about 2000 mPas at reaction temperature, in such a reactor leads, as a result of the significantly increased pressure drop, to such drastically reduced achievable conveying rates that an economically viable process regime is impossible. The alternatively possible use of solvents is typically undesired, since this firstly causes additional costs (lower reactor loading, recycling costs, etc.) and, secondly, the absence of solvent residues has to be ensured for many product applications, for example in the cosmetics or pharmaceutical industry, often down to the single-figure ppm range. The latter is usually possible in principle, but typically entails additional workup steps, for example distillation, extraction or evaporation, which take additional time, and therefore further increase the preparation costs and lower the space-time yields of the processes.

A further disadvantage of the fixed bed reactor lies in the sometimes inhomogeneous flow through the reactor with channel formation and the possibility of blockage of the cavities by suspended substances.

There is therefore still a need for reaction processes for heterogeneously catalysed preparation of carboxylic acid derivatives, particularly from high-viscosity mixtures, which overcome the disadvantages of the prior art.

It was therefore an object of the present invention to provide a universal process for heterogeneously catalysed preparation of carboxylic acid derivatives, which enables the solvent-free processing of low and higher-viscosity reaction mixtures with the simultaneous possibility of simple removal and reusability of the catalyst. The process should preferably be suitable for use of immobilized biocatalysts.

Further objects which are not stated explicitly are evident from the context of the description which follows, the examples and the claims.

It has been found that, surprisingly, this object is achieved by a reactor design in which a circulation reactor with a reaction vessel in which the heterogeneous catalyst is freely distributed in the reaction mixture and an additional gas input ensures the mixing in the reaction vessel is used.

The present invention therefore provides a process for preparing carboxylic acid derivatives, which utilizes this reactor design.

The process according to the invention is described by way of example hereinafter, without any intention that the invention be restricted to these illustrative embodiments. Where ranges, general formulae or compound classes are specified below, these shall encompass not just the corresponding ranges or groups of compounds which are mentioned explicitly, but also all sub-ranges and sub-groups of compounds which can be obtained by selecting individual values (ranges) or compounds. When documents are cited in the context of the present description, their contents shall be included fully in the disclosure-content of the present invention. When compounds, for example polyethers or polysiloxanes, which may have different units more than once, are described in the context of the present invention, they may occur in these compounds in random distribution (random oligomer) or in ordered form (block oligomer). Figures regarding the number of units in such compounds should be interpreted as the mean, averaged over all compounds of that type.

Figure 1:
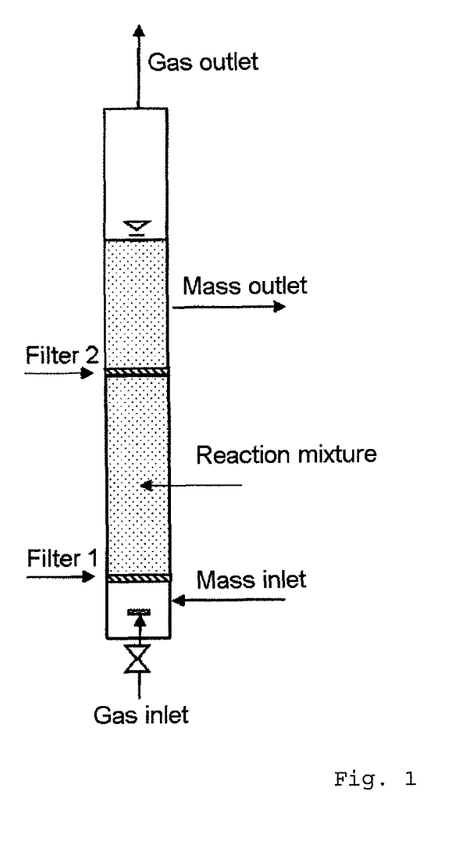
FIG. 1—depicts a reaction vessel with at least two outlets for the reaction medium, at least one gas outlet and at least one means of gas introduction.

In the process according to the invention, the catalyst used is used in a reaction vessel R, which is characterized in that at least two outlets for the reaction medium, at least one gas outlet and at least one means of gas introduction are present. In addition, a portion of the reaction vessel is delimited by suitable filters such that the catalyst can be used therein. At the same time, the catalyst should not be densely packed and the design of the reaction vessel must ensure that both gas flow and mass flow lead through the region or the regions which comprises or comprise the catalyst. A preferred embodiment of the reaction vessel R is shown in FIG. 1.

The gas introduction serves to mix the reaction mixture homogeneously, to keep the heterogeneous support suspended and, depending on the reaction being performed, to remove low-boiling reaction products, for example water in esterifications or lower alcohols in transesterification reactions of the corresponding esters, from the reaction mixture and hence to shift the equilibrium to the product side. Preferably in accordance with the invention, the gas outlet of the reaction vessel is connected to a condenser in order to be able to capture the low-boiling reaction products. Examples of inventive gas inlets are ring spargers, gas nozzles, ceramic filters, etc., which are generally familiar to the person skilled in the art.

According to the invention, the gases used may be those which do not enter into any reactions with the reactants, the catalyst or the reactor materials. Preference is given to using air, lean air, oxygen, nitrogen, noble gases or carbon dioxide. The gases used can be supplied from suitable pressure vessels, for example gas bottles, or by means of compressors. The waste air stream can be discharged or, by means of suitable measures, reused and circulated.

Figure 3:
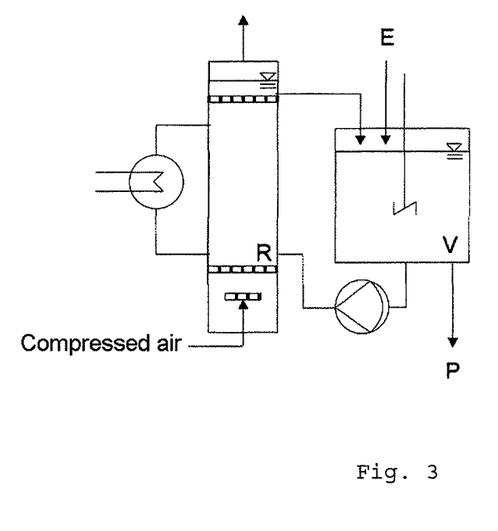
FIG. 3—depicts a reaction vessel which integrates a filter into the mass inlet.
Figure 4:
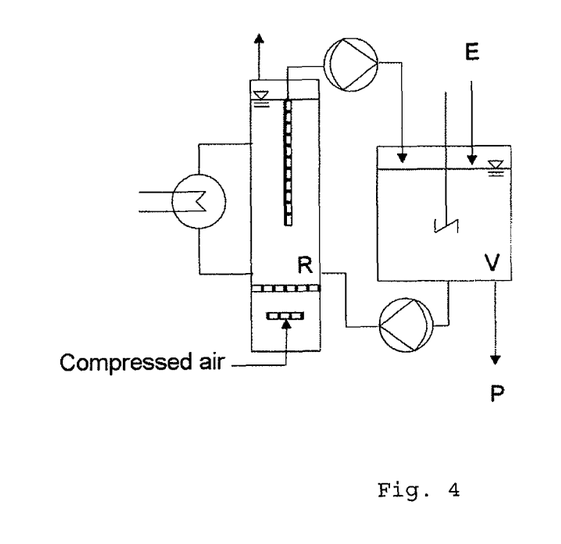
FIG. 4—depicts a reaction vessel which integrates a filter as a cartridge filter.

According to the invention, further embodiments of the reaction vessel R are possible. For example, it is possible to integrate the filter 1 into the mass inlet or to design it as a cartridge filter. Examples of such embodiments are shown in FIG. 3 and FIG. 4. Alternatively, the filter can also be integrated as a tube bundle or monolithic tube bundle. Alternative embodiments of the reaction vessel R may also be an airlift reactor, pressure loop reactor or mammoth loop reactor.

Figure 2:
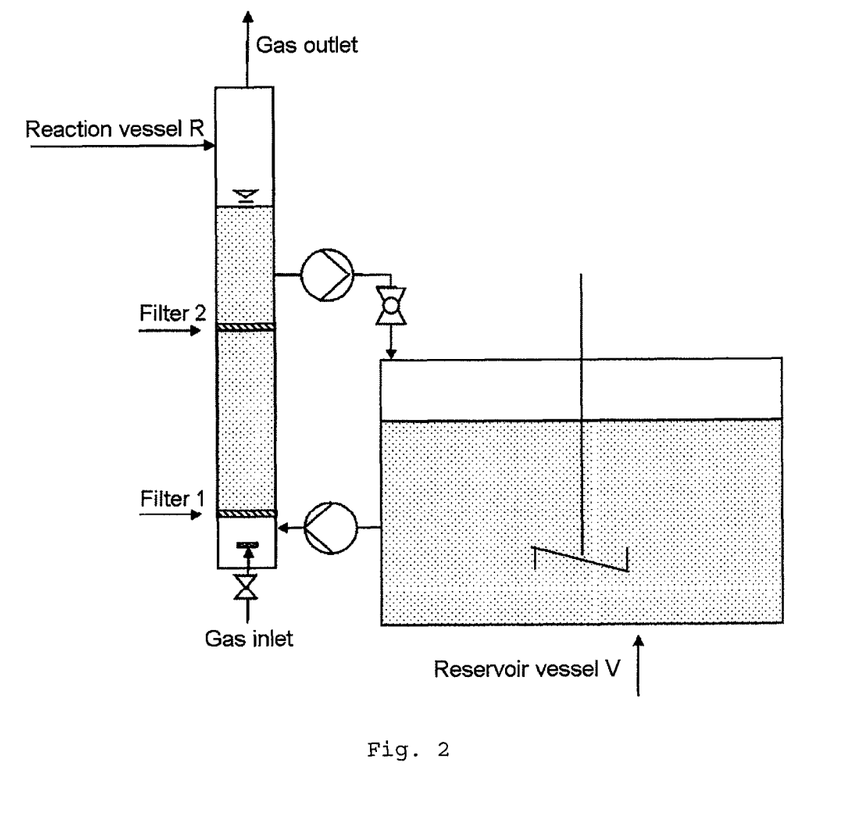
FIG. 2—depicts a reaction vessel with a reservoir vessel, lines and pumps.

According to the invention, in addition to the reaction vessel R, at least one reservoir vessel V is used. In one embodiment of the invention, a reservoir vessel equipped with at least two mass outlets is used. In this case, the reaction mixture is pumped from the reservoir vessel V through a suitable line into the reaction vessel R and, after flowing through the region containing the catalyst, pumped back into the reservoir vessel through a suitable line. For this purpose, at least one suitable pump between reservoir vessel V and reaction vessel R is required. Optionally, a further pump between reaction vessel R and reservoir vessel V can be operated, in which case the pump performance of the individual pumps should be balanced with respect to one another by means of appropriate control elements. A preferred embodiment of the overall system, consisting of reaction vessel R, reservoir vessel V, lines and pumps, is shown in FIG. 2.

The reservoir vessel V may optionally be equipped with a stirrer in order to improve the mixing of the reaction system. For the same reason, the feed line from the reservoir vessel V to the reaction vessel R may be interrupted with a further technical apparatus for improving the mixing, for example a disperser.

In a further embodiment of the invention, the reservoir vessel V is provided with the possibility of applying vacuum in order to further promote the removal of the low-boiling reaction products, for example water in esterifications or lower alcohols in transesterification reactions of the corresponding esters, from the reaction mixture. In the case of use of vacuum, it may be necessary to interrupt the line between reaction vessel R and reservoir vessel V with a second pump and a pressure retaining valve. Optionally, the removal of low-boiling reaction components can be accelerated further by further internals, for example falling-film evaporators.

The constituents of the inventive system, especially the reaction vessel R, the reservoir vessel V and the feed lines and removal lines can be provided with a means of thermostating, for example with a heater based on electricity, steam or thermal oil.

In a further particular embodiment, in addition to the reaction vessel R, two reservoir vessels V1 and V2 are used in a continuous preparation process. In this case, the reaction mixture is conveyed out of the reservoir vessel V1, which is provided with at least one mass outlet and if appropriate with a stirrer or another mixing unit, into the reaction vessel R as described above. After flowing through the region containing the catalyst, the reaction mixture is conveyed into the reservoir vessel V2.

In a further embodiment, the reaction mixture can be conveyed out of the reservoir vessel V2 through a second reaction vessel R2 into a reservoir vessel V3, in which case the reaction vessel R2 is constructed as described for vessel R1 and is filled with a catalyst, and reservoir vessel V2, like vessel V1, is provided with at least one mass outlet and if appropriate with a stirrer or another mixing unit.

The catalysts used in accordance with the invention may be those whose particle size is such that they can be retained in the reaction vessel without any great pressure drop using the customary available filter systems, i.e. larger than 0.5 µm, preferably larger than 5 µm, more preferably larger than 10 µm, especially larger than 25 µm.

They may be polymeric catalysts of appropriate particle size, or catalysts immobilized on suitable supports.

Examples of the polymeric catalysts are ion exchangers, for example sulphonated polystyrenes or zeolites.

According to the invention, the catalysts immobilized on suitable supports may be chemical catalysts or enzyme immobilizates.

Examples of chemical catalysts are support-bound Lewis acids and amphoteric hydroxides.

To produce the enzyme immobilizates, it is possible to use whole cells, resting cells, purified enzymes or cell extracts which comprise the enzymes in question or mixtures thereof. Preference is given to using hydrolytic enzymes, for example lipases, esterases or proteases, for example lipases from *Candida rugosa, Candida antarctica, Pseudomonas* sp., *Thermomyces langosiosus*, porcine pancreas, *Mucor miehei, Alcaligines* sp., cholesterolases from *Candida rugosa*, esterase from the porcine liver, particular preference to using lipases. Accordingly, the enzyme immobilizates preferably comprise enzymes from the class of the hydrolases, preferably lipases.

The supports used to immobilize the enzymes or microorganisms containing enzymes may be inert organic or inorganic supports. The inert supports used are preferably those particulate supports, or those present in the enzyme immobilizate are preferably those, which have a particle size distribution in which at least 90% of the particles have a particle size of 0.5 to 5000 μm, preferably of 10 μm to 2000 more preferably of 25 μm to 2000 μm. The organic supports used may especially be those which comprise or consist of polyacrylate, polymethacrylate, polyvinylstyrene, styrene-divinylbenzene copolymers, polypropylene, polyethylene, polyethylene terepthalate, PTFE and/or other polymers. The support material used may, depending on the enzyme to be immobilized, especially be acidic or basic ion exchange resins, for example sold under the tradenames DUOLITE A568, DUOLITE XAD 761, DUOLITE XAD 1180, DUOLITE XAD 7HP, AMBERLITE IR 120, AMBERLITE IR 400, AMBERLITE CG 50, AMBERLYST 15 (all products from Rohm and Haas), or LEWATIT CNP 105 and LEWATIT VP OC 1600 (products from Lanxess, Leverkusen, Germany). The inorganic supports used may be oxidic and/or ceramic supports known from the prior art. More particularly, the inorganic supports used may, for example, be the diatomaceous earth inorganic support sold under the tradename CELITE, zeolites, silica, controlled-pore glass (CPG) or other supports, as described, for example, in L. Cao, "Carrier-bound Immobilized Enzymes: Principles, Application and Design", Wiley-VCH: 2005, Weinheim, Germany. More preferably, the inert supports present in the enzyme immobilizate or the inert supports used to prepare the enzyme immobilizates consist of polyvinylstyrene, polymethacrylate or polyacrylate.

According to the invention, the immobilization on the particles can be effected covalently or noncovalently.

Examples of the enzyme immobilizates used in accordance with the invention are the enzyme immobilizates sold under the tradenames NOVOZYM 435, LIPOZYM RM IM or LIPOZYM TL IM from Novozymes A/S, Bagsvaerd, Denmark, or AMANO PS, from Amano, Japan.

The present invention thus provides a process for heterogeneously catalysed preparation of carboxylic acid derivatives using a reactor system, for example according to FIG. 2, comprising at least one reservoir vessel V, feed lines, at least one pump and a reaction vessel R, wherein a permanent gas flow through the reaction vessel R is applied through a gas feed line, and in which a reaction chamber in which the heterogeneous catalyst is not introduced in tightly packed form is delimited by at least two filters such that both the mass flow and the gas flow are passed through the reaction chamber.

The invention further provides a process in which the catalyst used is at least one enzyme, or microorganisms comprising at least one enzyme.

The invention further provides a process in which the enzymatic system is present in heterogeneously supported form on a solid.

The invention further provides a process in which the enzymatic catalyst is fixed covalently or noncovalently in particulate form on a support material.

The invention further provides a process in which the solid consists of a polymer based on polyacrylate, polymethacrylate, polyvinylstyrene, styrene-divinylbenzene copolymers, polypropylene, polyethylene, polyethylene terephthalate, or polytetrafluoroethylene or copolymers of these compounds or oxidic and/or ceramic supports.

The invention further provides a process in which the solid consists of an acidic or basic ion exchange resin.

The invention further provides a process in which the oxidic and/or ceramic support consists of CELITE, zeolites, silica or controlled-pore glass.

The invention further provides a process in which the support material has a mean particle size of greater than 0.5 μm.

The invention further provides a process in which the heterogeneous catalyst system is reused. In one embodiment of this aspect of the invention, reuse of the catalyst results in at least a 95% conversion rate for up to nine additional batches (up to ten total batches) where the concentration of the catalyst is 0.1 to 5 percent per weight of the total of reactants. In another embodiment of this aspect of the invention, reuse of the catalyst results in at least a 98.5% conversion rate for up to nine additional batches (up to ten total batches) where the concentration of the catalyst is 0.1 to 5 percent per weight of the total of reactants.

The invention further provides a process in which vacuum is applied at the reservoir vessel V.

The invention further provides a process in which the gas used is air, lean air, oxygen, nitrogen, noble gases or carbon dioxide, preferably air or nitrogen.

The invention further provides a process in which the reaction is performed at a temperature of 20° C. to 100° C.

Further subject-matter of the invention is evident from the wording of the claims.

According to the invention, the process is preferably used to perform conversions of the general formula I where
- $R_1$ is the acyl radical of linear, branched, saturated or unsaturated, optionally additionally substituted carboxylic acids having 2 to 30 carbon atoms,
- X is oxygen, sulphur or —NH—, preferably oxygen,
- $R_2$ is hydrogen or a linear or branched alkyl or alkenyl group having 1 to 3 carbon atoms,
- Y is oxygen, sulphur or —NH—, preferably oxygen or —NH—, more preferably oxygen,
- $R_3$ is a linear, branched, saturated or unsaturated, optionally additionally substituted alkyl radical having 2 to 30 carbon atoms.

According to the invention, the optional additional substituents of the $R_1$ and $R_3$ radicals may each independently, for example, be hydroxyl groups, ester groups, polyester groups, carbonate groups, polycarbonate groups, ether groups, polyether groups, urethane groups, polyurethane groups, amide groups, polyamide groups, alkylamine groups, dialkylamine groups, halides, siloxane groups, ester groups of inorganic acids, sulphates, phosphates or similar moieties.

In a preferred embodiment, $R_1$ is the acyl radical of commercially available acids, for example acetic acid, propanoic acid, butanoic acid, pentanoic acid, chloroacetic acid, trifluoroacetic acid, ethylhexanoic acid, isononanoic acid, isotridecanoic acid or isostearic acid.

In a further preferred embodiment, the $R_1$ radicals used are acyl radicals of natural fatty acids based on natural vegetable or animal oils. Preference is given to using natural fatty acids, for example caproic acid, caprylic acid, capric acid, lauric acid, myristic acid, palmitic acid, palmitoleic acid, isostearic acid, stearic acid, 12-hydroxystearic acid, dihydroxystearic acid, oleic acid, linoleic acid, petroselic acid, elaidic acid, arachic acid, behenic acid, erucic acid, gadoleic acid, linolenic acid, eicosapentaenoic acid, docosahexaenoic acid or arachidonic acid, alone or in a mixture. The $R_1$ radical may likewise be the acyl radical of polycondensation products of hydroxy-functional acids, for example poly-12-hydroxystearic acid or polyricinoleic acid. The acyl radicals used as the $R_1$ radical may be technical-grade mixtures, for example mixtures of natural fatty acids, for example rapeseed oil fatty acid, soybean oil fatty acid, sunflower oil fatty acid, tallow oil fatty acid, palm oil fatty acid, palm kernel oil fatty acid, coconut fatty acid, which, depending on their specific source and the purification processes used, may be subject to variations in their exact composition, and may also comprise typical secondary constituents, such as unsaturated, functionalized or branched components. In addition, it is also possible to use mixtures of acids of another origin, for example based on petrochemical processes.

In a further preferred embodiment, the $R_3$ radicals used are, for example, the hydrocarbon radicals of propanol, butanol, pentanol, hexanol, octanol or isomers thereof, such as isopropanol, isobutanol, 2-ethylhexanol, isononyl alcohol, isotridecyl alcohol, polyhydric alcohols such as 1,6-hexanediol, 1,2-pentanediol, dihydroxyacetone, 1,2-propylene glycol, 1,3-propylene glycol, neopentyl glycol, trimethylolpropane, pentaerythritol, sorbitol, glycerol, diglycerol, triglycerol, polyglycerol, ethylene glycol, diethylene glycol, triethylene glycol, polyethylene glycol, or amino-functionalized alcohols, such as N,N-dimethylethanolamine. Further examples are the hydrocarbon radicals of alcohols which are prepared by known processes from monobasic fatty acids based on natural vegetable or animal oils having 6 to 30 carbon atoms, especially having 8 to 22 carbon atoms, for example caproic acid, caprylic acid, capric acid, lauric acid, myristic acid, palmitic acid, palmitoleic acid, isostearic acid, stearic acid, 12-hydroxystearic acid, dihydroxystearic acid, oleic acid, linoleic acid, petroselic acid, elaidic acid, arachic acid, behenic acid, erucic acid, gadoleic acid, linolenic acid, eicosapentaenoic acid, docosahexaenoic acid or arachidonic acid, alone or in a mixture.

Examples of the inventive polyether-substituted $R_3$ radicals are the alkyl radicals of polyethylene glycol, polypropylene glycol, polybutylene glycol, polystryene oxide or copolymers of at least two monomers from the group of ethylene glycol, propylene glycol, butylene glycol, stryrene oxide and polyglycerol. These polyether-substituted radicals may in turn again bear substituents on further OH groups, for example alkyl or alkenyl ethers or alkyl esters.

Examples of the inventive polyester-substituted $R_3$ radicals are polymers which bear free OH groups and are based on ϵ-caprolactone or γ-valerolactone, for example sold under the tradename PLACCEL L212AL from Daicel.

Examples of the inventive polycarbonate-substituted radicals are polymers which bear free OH groups and are based on dialkyl carbonate and dihydroxyalkyl units, for example sold under the tradename PLACCEL CD220 from Daicel.

Examples of the inventive polysiloxane-substituted $R_3$ radicals are organomodified polysiloxanes bearing free alkyl-OH groups, as obtainable, for example, by hydrosilylating SiH-siloxanes with terminally unsaturated alcohols by methods known to those skilled in the art. In particular, it is possible here to use linear alkenols, such as 5-hexen-1-ol, or allyloxy derivatives such as allyloxyethanol, allylglycerol, allylpolyglycerol, allyltrimethylolpropane, allylpolyethylene glycol, allylpolypropylene glycol, or allylpolyethylene glycolpolyproypylene glycol copolymers.

Examples of the inventive polysiloxane-substituted $R_1$ radicals are organomodified polysiloxanes bearing free carboxyl groups, as obtainable, for example, by hydrosilylating SiH-siloxanes with terminally unsaturated acids by methods known to those skilled in the art. In particular, it is possible here to use acrylic acid, methacrylic acid or undec-10-enoic acid.

The examples which follow are intended to illustrate the present invention in detail, without restricting the scope of protection, which is evident from the description and the claims.

MATERIALS AND METHODS

NOVOZYM 435 (NZ435) is the tradename of a commercial enzyme immobilizate from Novozymes A/S, Bagsvaerd/Denmark, a lipase B from *C. antarctica* immobilized by adsorption on a polymethacrylate.

EXAMPLES

Example 1

Test Reactor Construction

Figure 5:
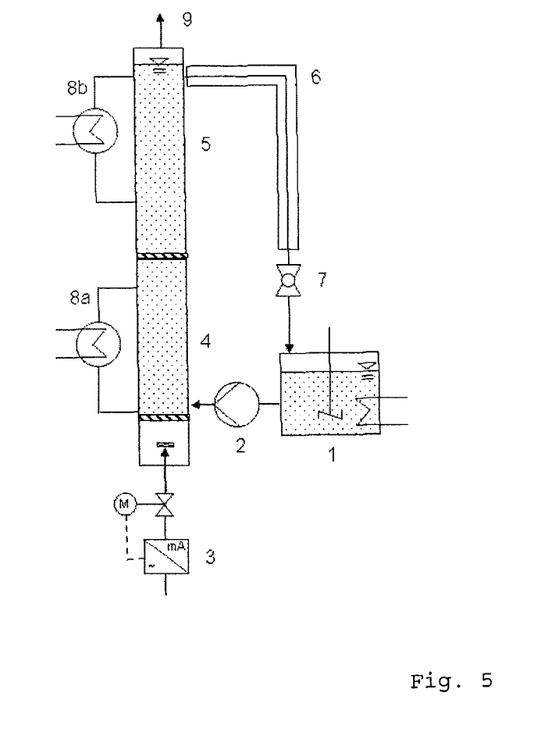
FIG. 5—depicts the test reactor of Example 1.

The construction of the illustrative test reactor is shown schematically in FIG. 5. The circulation reactor consists of a thermostated (8) reaction vessel (4, 5) having a length of 60 cm and a diameter of 2.5 cm. The reaction vessel is separated into two regions (4, 5) by a centrally mounted, removable metal screen having a pore size of 50 μm. A further metal screen delimits the reaction vessel at the bottom and serves as a gas distributor. The heterogeneous catalyst is thus retained in the lower region of the reaction vessel (4). The reaction mixture is pumped from the stirred reservoir vessel (1) above the gas distributor into the reaction vessel (4) with the aid of a peristaltic pump (2). At the same time, gas is introduced (3) into the reaction vessel from below in a controlled manner. The reaction mixture first fills the lower region (4), then the upper region (5), the catalyst being retained by the screens. When it reaches the overflow, the reaction mixture flows through a thermostated line (6, 7) back into the reservoir vessel (1). The gas introduced escapes via the gas outlet (9).

The discharge of the water of reaction, and of the other low-boiling reaction products, and the mixing of the reactants, are effected in the reaction vessel by the ascending gas bubbles. At the same time, the reservoir vessel is stirred, and it is additionally possible to apply vacuum to the reservoir vessel for accelerated discharge of the low-boiling reaction products.

Example 2

Synthesis of Myristyl Myristate 329 g of myristyl alcohol and 351 g of myristic acid were heated to 60° C. in a 1 l reservoir vessel and mixed by means of a magnetic stirrer (viscosity of the mixture at 60° C. approx. 6 mPas). The lower region of the reaction vessel was initially charged with 2.7 g of NOVOZYM 435 and the entire reaction vessel was heated to 60° C. The compressed air introduction was regulated to 0.4 l/min and then the peristaltic pump was set to ~20 ml/min and switched on. The reflux was heated to 60° C. The course of the reaction was monitored for ~25 h, and a conversion of 99.3% based on the fatty acid was achieved.

TABLE 1

Conversion data for Example 2:

| Time [min] | Conversion [%] |
|---|---|
| 0 | 0 |
| 30 | 25.8% |
| 60 | 46.9% |
| 124 | 74.6% |
| 169 | 85.7% |
| 223 | 92.6% |
| 300 | 96.5% |
| 346 | 97.4% |
| 1442 | 99.3% |

Example 3

Reuse of the Catalyst

Analogously to Example 2, several reactions for synthesis of myristyl myristate are performed reusing the enzyme catalyst without intermediate purification, and the conversion after 1 and 24 hours is determined. 10 repetitions were carried out.

TABLE 2

Conversion data for Example 3

| Repetition | Conversion after 1 h | Conversion after 24 h |
|---|---|---|
| 1 | 46.9% | 99.3% |
| 2 | 45.3% | 99.6% |
| 3 | 46.2% | 99.3% |
| 4 | 44.7% | 99.5% |
| 5 | 47.1% | 99.1% |
| 6 | 46.9% | 99.2% |
| 7 | 44.7% | 99.0% |
| 8 | 47.4% | 98.9% |
| 9 | 45.2% | 99.2% |
| 10 | 44.3% | 99.0% |

Example 4

Synthesis of polyglycerol-3 laurate 350 g of polyglycerol-3 (from Daicel) and 280 g of lauric acid were heated to 80° C. in a 1 l reservoir vessel and mixed by a mechanical stirrer (viscosity of the mixture at 60° C. approx. 2000 mPas). The lower region of the reaction vessel was initially charged with 5.5 g of NOVOZYM 435 and the entire reaction vessel was heated to 80° C. The compressed air introduction was regulated to 1.20 l/min and then the peristaltic pump was set to ~20 ml/min and switched on. The reflux was heated to 80° C. The course of the reaction was monitored for 24 hours, and a conversion of 96.7% based on the fatty acid was achieved.

TABLE 3

Conversion data for Example 4:

| Time [min] | Conversion [%] |
|---|---|
| 0 | 0.0 |
| 15 | 14.3 |
| 30 | 27.9 |
| 60 | 49.7 |
| 123 | 72.7 |
| 244 | 90.3 |
| 1440 | 96.7 |

Having thus described in detail various embodiments of the present invention, it is to be understood that the invention defined by the above paragraphs is not to be limited to particular details set forth in the above description as many apparent variations thereof are possible without departing from the spirit or scope of the present invention.

The invention claimed is:

1. A process for heterogeneously catalysed preparation of a carboxylic acid derivative, selected from the group consisting of esters, thioesters, and amides, by reacting a carboxylic acid with a corresponding reactant sufficient to form the carboxylic acid derivative therewith, the process comprising:
 (a) utilizing a reactor system comprising:
   at least one reservoir vessel (V);
   a reaction vessel (R) comprising a reaction chamber;
   reaction medium feed lines which connect the reservoir vessel (V) to the reaction vessel (R); and
   at least one pump operably connected to at least one of the reaction medium feed lines;
 (b) providing a heterogeneous catalyst in the reaction chamber, the heterogeneous catalyst comprising at least one enzyme or comprising microorganisms comprising at least one enzyme;
 (c) applying, through a gas feed line, a permanent gas flow through the reaction vessel (R);
 (d) applying a reaction medium to the reaction chamber, the reaction medium comprising the carboxylic acid and the corresponding reactant sufficient to form the carboxylic acid derivative; and (e) reacting the reaction medium in the presence of the heterogeneous catalyst and the gas flow, so as to prepare the carboxylic acid derivative;

wherein the heterogeneous catalyst, which is not introduced in tightly packed form, is delimited in the reaction chamber between at least two filters, such that both the mass flow of the reaction medium and the gas flow are passed through the reaction chamber.

2. The process according to claim 1;
wherein the enzyme or microbial catalyst is supported on a solid.

3. The process according to claim 2;
wherein the enzymatic or microbial catalyst is fixed covalently or noncovalently in particulate form on the solid.

4. The process according to claim 3;
wherein the solid comprises at least one substance selected from the group consisting of:
  polymers selected from the group consisting of polyacrylate, polymethacrylate, polyvinylstyrene, styrene-divinylbenzene copolymers, polypropylene, polyethylene, polyethylene terephthalate, polytetrafluoroethylene, and copolymers of these compounds; and
  oxidic and ceramic supports.

5. The process according to claim 4;
wherein the solid comprises an acidic or basic ion exchange resin.

6. The process according to claim 4;
wherein the solid comprises a polymethacrylate polymer.

7. The process according to claim 6;
wherein the solid is in the form of support material having a mean particle size of greater than 0.5 μm.

8. The process according to claim 7;
wherein the heterogeneous catalyst is reused.

9. The process according to claim 8, further comprising:
applying a vacuum pressure at the reservoir vessel (V).

10. The process according to claim 9;
wherein the gas comprises at least one component selected from the group consisting of air, lean air, oxygen, nitrogen, noble gases, and carbon dioxide.

11. The process according to claim 10;
wherein the reaction is performed at a temperature of 20° C. to 100° C.

12. The process according to claim 2;
wherein the solid comprises at least one substance selected from the group consisting of;
  polymers selected form the group consisting of polyacrylate, polymethacrylate, polyvinylstyrene, styrene-divinylbenzene copolymers, polypropylene, polyethylene, polyethylene terephthalate, polytetrafluoroethylene, and copolymers of these compounds; and
  oxidic and ceramic supports.

13. The process according to claim 2;
wherein the solid consists of an acidic or basic ion exchange resin.

14. The process according to claim 2; wherein the oxidic and/or ceramic support consists of diatomite, zeolites, silica or controlled-pore glass.

15. The process according to claim 2;
wherein the solid is in the form of support material with a mean particle size of greater than 0.5 μm.

16. The process according to claim 1;
wherein the heterogeneous catalyst is reused.

17. The process according to claim 1, further comprising:
applying a vacuum pressure at the reservoir vessel (V).

18. The process according to claim 1;
wherein the gas comprises at least one component selected from the group consisting of air, lean air, oxygen, nitrogen, noble gases, and carbon dioxide.

19. The process according to claim 1;
wherein the reaction is performed at a temperature of 20° C. to 100° C.

* * * * *